(12) United States Patent
Nishiuchi et al.

(10) Patent No.: US 8,703,912 B2
(45) Date of Patent: Apr. 22, 2014

(54) PROCESSES FOR REMOVAL OF DIBENZOFULVENE

(75) Inventors: Yuji Nishiuchi, Osaka (JP); Terutoshi Kimura, Osaka (JP)

(73) Assignee: Ajinomoto Co., Inc., Tokyo (JP)

( * ) Notice: Subject to any disclaimer, the term of this patent is extended or adjusted under 35 U.S.C. 154(b) by 396 days.

(21) Appl. No.: 13/020,838

(22) Filed: Feb. 4, 2011

(65) Prior Publication Data

US 2011/0190475 A1  Aug. 4, 2011

Related U.S. Application Data

(63) Continuation of application No. PCT/JP2009/063959, filed on Aug. 6, 2009.

(30) Foreign Application Priority Data

Aug. 6, 2008  (JP) ................................. 2008-203635

(51) Int. Cl.
  *C07K 1/00*  (2006.01)
(52) U.S. Cl.
  USPC ............ 530/335; 530/333; 530/337; 530/344
(58) Field of Classification Search
  USPC .................................. 530/335, 333, 337, 344
  See application file for complete search history.

(56) References Cited

U.S. PATENT DOCUMENTS

| 2002/0058788 | A1   | 5/2002  | Sheppeck, II          |
|--------------|------|---------|-----------------------|
| 2007/0270573 | A1   | 11/2007 | Collins               |
| 2012/0061614 | A1 * | 3/2012  | Calabro et al. ........ 252/184 |
| 2012/0063979 | A1 * | 3/2012  | Kortunov et al. ....... 423/228 |
| 2012/0063980 | A1 * | 3/2012  | Kortunov et al. ....... 423/229 |

FOREIGN PATENT DOCUMENTS

WO    WO 99/48513 A1    9/1999

OTHER PUBLICATIONS

Chaturvedi (Current Organic Chemistry 15, 1593-1624, 2011).*
Chaturvedi (Current Organic Synthesis 4(3), 308-320(13), 2007).*
Sheppeck (Tetrahedron Letters 41, 5329-5333, 2000).*
Yamada (Chem. Mater., 19, (5), 967-969, 2007).*
Wright (J Am Chem Soc 70, 3865-3866, 1948).*
Shirono (Journal of Chemical and Engineering Data 53, 1867-1871, 2008).*
Vonderheiden, Frederick (Journal of Chemical and Engineering Data 8, 20-1, 1963).*
Buell (Journal of Chemical and Engineering Data 7(2), 187-189, 1962).*
English abstract of Hironao (JP 2007-08887, issued Jan. 2007).*
Extended Search Report issued Feb. 20, 2013 in European Patent Application No. 09805034.7.
International Search Report issued Sep. 8, 2009, in International application No. PCT/JP2009/063959.

* cited by examiner

*Primary Examiner* — David Lukton
(74) *Attorney, Agent, or Firm* — Oblon, Spivak, McClelland, Maier & Neustadt, L.L.P.

(57) ABSTRACT

A dibenzofulvene amine adduct is removed by contacting a reaction mixture containing the dibenzofulvene amine adduct, which is obtained by reacting, for deprotection, an amino acid compound protected with an Fmoc group with an amine compound containing a nitrogen atom which is bonded to at least one hydrogen atom, with carbon dioxide, and removing the carbonate of the dibenzofulvene amine adduct. Alternatively, a dibenzofulvene amine adduct is removed by mixing a reaction mixture during a deprotection reaction of the amino acid compound protected with an Fmoc group, or after the reaction with an amine compound containing a nitrogen atom which is bonded to at least one hydrogen atom to give a mixture containing the dibenzofulvene amine adduct, contacting the mixture with carbon dioxide, and removing the carbonate of the dibenzofulvene amine adduct.

24 Claims, No Drawings

PROCESSES FOR REMOVAL OF DIBENZOFULVENE

CROSS REFERENCES TO RELATED APPLICATIONS

This application is a continuation of International Patent Application No. PCT/JP2009/063959, filed on Aug. 6, 2009, and claims priority to Japanese Patent Application No. 2008-203635, filed on Aug. 6, 2008, both of which are incorporated herein by reference in their entireties.

BACKGROUND OF THE INVENTION

1. Field of the Invention

The present invention relates to methods for efficient removal of a dibenzofulvene amine adduct generated as a by-product during deprotection of an amino acid compound protected with an Fmoc (9-fluorenylmethoxycarbonyl) group and the like.

2. Discussion of the Background

The Fmoc group is an amino-protecting group and is widely used since it provides many advantages such as suitable liposolubility imparted to the protected compound to facilitate handling, easy tracking of reaction utilizing imparted UV absorption, stability in the neutral to acidic range, easy deprotection under mild reaction conditions with amine and the like. Particularly, it is an important protecting group of amino group of amino acid and peptide in peptide synthesis.

During removal of the Fmoc group, an adduct of dibenzofulvene with amine, which is a deprotecting reagent, (hereinafter to be sometimes referred to as "dibenzofulvene amine adduct" in the present specification) is by-produced. Particularly in the peptide synthesis, the dibenzofulvene amine adduct needs to be efficiently removed, since it possibly causes side reactions such as 9-fluorenylmethylation and the like, when the dibenzofulvene amine adduct remains in the next step. However, the dibenzofulvene amine adduct is highly liposoluble, and cannot be removed by washing with water and the like of the reaction mixture.

In peptide synthesis, the Fmoc group is mainly utilized as a protecting group for a solid phase synthesis method, which can easily remove a dibenzofulvene amine adduct by washing a solid support. However, the solid phase method has problems in scaling up and reactivity, since the reaction is limited to the surface of a solid support.

On the other hand, a Boc (tert-butoxycarbonyl) group capable of removing a by-product of deprotection as a gas (isobutene, carbon dioxide) is mainly utilized for a liquid phase peptide synthesis method, since dibenzofulvene amine adduct cannot be easily removed. However, when a peptide containing a sulfur-containing amino acid such as cysteine, methionine and the like is to be synthesized, what is called a Boc method, wherein a Boc group is used at the N-terminal and a Z group is used in combination for the protection of a functional group of an amino acid side chain or the C-terminal, cannot be employed, since the sulfur-containing amino acid poisons catalysts and the Z group cannot be deprotected with a catalytic reduction. Thus, use of the Fmoc group as an N-terminal protecting group is sometimes desired.

In view of such background, development of a liquid phase method permitting easy scaling up and suitable for industrial production of peptide pharmaceutical products and the like is desired, which can efficiently remove dibenzofulvene amine adduct when the Fmoc group is used as a protecting group.

Jikken Kagaku Koza fifth edition, (Japan), MARUZEN CO., LTD., published on Mar. 31, 2005, vol. 16, page 272, describes a method for removal of a dibenzofulvene amine adduct in the liquid phase peptide synthesis, which includes adding a hydrocarbon solvent such as hexane and the like for trituration of a residue obtained by concentrating a reaction extract to dryness, thereby dissolving a dibenzofulvene amine adduct in the solvent, and isolating the deprotected peptide as crystals.

However, this method is poor in operability, sometimes fails to reproduce at a large scale, and is unsuitable for industrial production. In addition, when a desired deprotected peptide is an oily substance, this method cannot be used, since it requires crystallization of the peptide. Furthermore, the method is associated with problems of low recovery rate and the like due to dissolution of peptide itself in a hydrocarbon solvent when the peptide chain is short.

SUMMARY OF THE INVENTION

Problems to be Solved by the Invention

An object of the present invention is to provide a method for efficient removal of a dibenzofulvene amine adduct generated as a by-product after deprotection when the Fmoc group is used as a protecting group, particularly, a method applicable to industrial production by liquid phase peptide synthesis, and further, an operation leading to a method enabling one-pot synthesis.

Means of Solving the Problems

The present inventors have conducted intensive studies regarding a method for removal of a dibenzofulvene amine adduct in an attempt to solve the above-mentioned problems, and found that the dibenzofulvene amine adduct can be conveniently removed by contacting a mixture containing the dibenzofulvene amine adduct with carbon dioxide to give carbonate, which resulted in the completion of the present invention.

Accordingly, the present invention encompasses the following.

[1] A method for removal of a dibenzofulvene amine adduct from a reaction mixture obtained by reacting, for deprotection, an amino acid compound protected with an Fmoc group with an amine compound containing a nitrogen atom which is bonded to at least one hydrogen atom, said method comprising:

(i) contacting said reaction mixture with carbon dioxide, to obtain a carbonate of said dibenzofulvene amine adduct; and (ii) removing said carbonate of said dibenzofulvene amine adduct from said reaction mixture.

[2] A method for removal of dibenzofulvene, produced by deprotection of an amino acid compound protected with an Fmoc group, from a reaction mixture, which comprises:

(i) mixing a reaction mixture formed by deprotection of an amino acid compound protected with an Fmoc group with an amine compound containing a nitrogen atom which is bonded to at least one hydrogen atom to give a mixture containing a dibenzofulvene amine adduct;

(ii) contacting said mixture with carbon dioxide, to obtain a carbonate of said dibenzofulvene amine adduct; and (iii) removing said carbonate of said dibenzofulvene amine adduct from said reaction mixture.

[3] A method of the above-mentioned [1], comprising precipitating said carbonate of said dibenzofulvene amine adduct in a solvent containing at least one member selected from the group consisting of acetic acid ester, chloroform, methylene chloride, tetrahydrofuran, acetonitrile, acetone, ether, and a mixture thereof.

[4] A method of the above-mentioned [3], comprising removing said carbonate of said dibenzofulvene amine adduct by filtration.

[5] A method of the above-mentioned [1], wherein said amine compound containing a nitrogen atom which is bonded to at least one hydrogen atom is a diamine.

[6] A method of the above-mentioned [5], wherein said amine compound containing a nitrogen atom which is bonded to at least one hydrogen atom is selected from the group consisting of 4-aminomethylpiperidine, 4-dimethylaminopiperidine, 1,5-diaminopentane and 1,2-diaminocyclohexane.

[7] A method of the above-mentioned [1], wherein said amino acid compound protected with an Fmoc group is an amino acid ester protected with an Fmoc group, an amino acid amide protected with an Fmoc group, or a peptide protected with an Fmoc group.

[8] A method of producing peptide by a liquid phase synthesis method, comprising the method of the above-mentioned [7].

A method of the above-mentioned [8], comprising:

(1) condensing a C-protected peptide, a C-protected amino acid or a C-protected amino acid amide with N-Fmoc amino acid in the presence of a condensing agent; and/or (2) condensing a C-protected peptide, a C-protected amino acid or a C-protected amino acid amide with an N-Fmoc amino acid activated ester.

[10] A method of the above-mentioned [9], wherein said condensing a C-protected peptide, a C-protected amino acid, or a C-protected amino acid amide with N-Fmoc amino acid in the presence of a condensing agent, (1), is performed in the further presence of an activator.

[11] A method of the above-mentioned [9], wherein an intermediate peptide obtained by a method which comprises reacting an amino acid compound protected with an Fmoc group with an amine compound containing a nitrogen atom which is bonded to at least one hydrogen atom, to obtain an intermediate peptide, without isolation as a solid, is:

(1) condensed with N-Fmoc amino acid in the presence of a condensing agent; and/or (2) condensed with an N-Fmoc amino acid activated ester.

[12] A method of the above-mentioned (8), which is performed as a one-pot synthesis.

[13] A method for preparation of a peptide, comprising:

(i) reacting a first amino acid compound which is N-protected with an Fmoc group with a second amino acid compound which is N-unprotected, to obtain a third amino acid compound which is N-protected with an Fmoc group;

(ii) reacting said third amino acid compound with an amine compound containing a nitrogen atom which is bonded to at least one hydrogen atom to give a first reaction mixture which comprises a fourth amino acid compound which is N-unprotected and a dibenzofulvene amine adduct;

(iii) contacting said first reaction mixture with carbon dioxide, to obtain a second reaction mixture which comprises said fourth amino acid compound which is N-unprotected and a carbonate of said dibenzofulvene amine adduct; and (iv) removing said carbonate of said dibenzofulvene amine adduct from said second reaction mixture, to obtain a third reaction mixture which comprises said fourth amino acid compound which is N-unprotected; and (v) reacting said fourth amino acid compound which is N-unprotected with a fifth amino acid compound which is N-protected with an Fmoc group to obtain a sixth amino acid compound which is N-protected with an Fmoc group.

[14] A method of the above-mentioned [13], comprising precipitating said carbonate of said dibenzofulvene amine adduct in a solvent containing at least one member selected from the group consisting of acetic acid ester, chloroform, methylene chloride, tetrahydrofuran, acetonitrile, acetone, ether, and a mixture thereof.

[15] A method of the above-mentioned [13], comprising removing said carbonate of said dibenzofulvene amine adduct by filtration.

[16] A method of the above-mentioned [13], wherein said amine compound containing a nitrogen atom which is bonded to at least one hydrogen atom is a diamine.

[17] A method of the above-mentioned [13], wherein said amine compound containing a nitrogen atom which is bonded to at least one hydrogen atom is selected from the group consisting of 4-aminomethylpiperidine, 4-dimethylaminopiperidine, 1,5-diaminopentane and 1,2-diaminocyclohexane.

[18] A method of the above-mentioned [13], wherein said first amino acid compound which is N-protected with an Fmoc group is an amino acid ester protected with an Fmoc group, an amino acid amide protected with an Fmoc group, or a peptide protected with an Fmoc group.

[19] A method of the above-mentioned [13], wherein said fifth amino acid compound which is N-protected with an Fmoc group is an amino acid ester protected with an Fmoc group, an amino acid amide protected with an Fmoc group, or a peptide protected with an Fmoc group.

[20] A method of the above-mentioned [13], wherein said second amino acid compound which is N-unprotected is a C-protected peptide, a C-protected amino acid, or a C-protected amino acid amide.

Effect of the Invention

The present invention provides a method for convenient removal of a dibenzofulvene amine adduct generated as a by-product during deprotection of an Fmoc group. The method does not require complicated operations such as trituration of crystals and the like, and can also be applied easily to large-scale reactions. As a result, the Fmoc group can be easily utilized for industrial production, which strikingly broadens the options of the production methods of compounds requiring protection of an amino group.

Particularly, when the method of the present invention is applied to a liquid phase peptide synthesis method, dibenzofulvene amine adduct are conveniently removed by filtration alone, and peptide with an unprotected N-terminal obtained by deprotection can be conveniently purified as necessary by further converting to hydrochloride and the like. As such, a peptide elongation reaction in the next step can be continuously performed, thus enabling one-pot synthesis of peptide, which is particularly preferable for industrial production.

DETAILED DESCRIPTION OF THE PREFERRED EMBODIMENTS

The symbols and abbreviations used in the present specification mean the following.

(1) Boc: tert-butoxycarbonyl
(2) Z: benzyloxycarbonyl
(3) Fmoc: 9-fluorenylmethoxycarbonyl
(4) Bsmoc: 1,1-dioxobenzo[b]thiophen-2-ylmethoxycarbonyl
(5) Alloc: allyloxycarbonyl
(6) Ac: acetyl
(7) Pbf: 2,2,4,6,7-pentamethyldihydrobenzofuran-5-sulfonyl
(8) Me: methyl (9) Et: ethyl
(10) iPr: isopropyl
(11) tBu: tert-butyl
(12) Bzl: benzyl
(13) Fm: 9-fluorenylmethyl
(14) Trt: trityl
(15) Dpm: diphenylmethyl
(16) Bpr: 1,1-dimethyl-2-phenyl-ethyl
(17) Dmb: 2,4-dimethoxybenzyl
(18) HOBt: 1-hydroxybenzotriazole
(19) 6-Cl-HOBt (HOCt): 6-chloro-1-hydroxybenzotriazole
(20) HOAt: 1-hydroxy-7-azabenzotriazole
(21) HOOBt (HODhbt): 3-hydroxy-3,4-dihydro-4-oxo-1.2.3-benzotriazine
(22) HOSu: N-hydroxysuccinimide
(23) HOPht: N-hydroxyphthalimide
(24) HONb: N-hydroxy-5-norbornene-2,3-dicarboxyimide
(25) Bt: benzotriazol-1-yl
(26) Ct: 6-chlorobenzotriazol-1-yl
(27) At: 7-azabenzotriazol-1-yl
(28) Dhbt: 3,4-dihydro-4-oxo-1.2.3-benzotriazin-3-yl
(29) Su: succinimidoyl
(30) Pht: phthalimidoyl
(31) Nb: 5-norbornene-2,3-dicarboxyimidoyl
(32) DCC: dicyclohexylcarbodiimide
(33) EDC: 1-ethyl-3-(3-dimethylaminopropyl)-carbodiimide
(34) EDC.HCl: 1-ethyl-3-(3-dimethylaminopropyl)-carbodiimide hydrochloride
(35) DIPC: diisopropylcarbodiimide
(36) BOP: 1-benzotriazolyloxy-tris-dimethylamino-phosphonium hexafluorophosphate
(37) PyBOP: 1-benzotriazolyloxy-tris-pyrrolidino-phosphonium hexafluorophosphate
(38) PyBroP: bromo-tris-pyrrolidino-phosphonium hexafluorophosphate
(39) HBTU: O-(benzotriazol-1-yl)-1,1,3,3-tetramethyluronium hexafluorophosphate
(40) TBTU: O-benzotriazol-1-yl-1,1,3,3-tetramethyluronium tetrafluoroborate
(41) HCTU: O-(6-chlorobenzotriazol-1-yl)-1,1,3,3-tetramethyluronium hexafluorophosphate
(42) HATU: O-(7-azabenzotriazol-1-yl)-1,1,3,3-tetramethyluronium hexafluorophosphate
(43) CDI: carbonyldiimidazole
(44) DBU: 1,8-diazabicyclo[5,4,0]-7-undecene
(45) DMT-MM: 4-(4,6-dimethoxy-1,3,5-triazin-2-yl)-4-methylmorpholinium chloride
(46) $AA_n$: amino acid residue (subscript n is any integer of 1 or above, which shows the order from peptide C-terminal)
(47) $PG_0$: protecting group of C-terminal carboxyl group or C-terminal amide group of peptide
(48) $PG_n$: amino-protecting group (subscript n is any integer of 1 or above, which is a protecting group of amino group of $AA_n$)
(49) HOE: activator
(50) E: activated ester group
(51) Gly: glycine
(52) Ala: alanine
(53) Val: valine
(54) Leu: leucine
(55) Ile: isoleucine
(56) Met: methionine
(57) Phe: phenylalanine
(58) Tyr: tyrosine
(59) Trp: tryptophan
(60) His: histidine
(61) Lys: lysine
(62) Arg: arginine
(63) Ser: serine
(64) Thr: threonine
(65) Asp: aspartic acid
(66) Glu: glutamic acid
(67) Asn: asparagine
(68) Gln: glutamine
(69) Cys: cysteine
(70) Pro: proline
(71) Orn: ornithine
(72) Sar: sarcosine
(73) β-Ala: β-alanine
(74) GABA: γ-aminobutyric acid
(75) Dap: 2,3-diaminopropionic acid Examples of the protecting group of the C-terminal carboxyl group for $PG_0$ include alkyl groups such as Me, Et, iPr, tBu and the like, Z, Fm, Trt, Dpm, Bpr, 1-1-dimethylbenzyl, dimethylphenyl and the like.

Examples of the protecting group of the C-terminal amide group for $PG_0$ include Dmb, bis(4-methoxyphenyl)methyl, trityl and the like.

Examples of the amino-protecting group for $PG_n$ include Boc, Z, Fmoc, Bsmoc, Alloc, Ac and the like.

The activated ester group for E means a group which is easily dissociated as "EO$^-$" upon nucleophilic attack by an amino group and can produce an amide bond, and examples thereof include Bt, Ct, At, OBt, Su, Pht, Nb, pentafluorophenyl and the like.

1. Method for Removal of Dibenzofulvene-Amine

The method for removal of dibenzofulvene-amine of the present invention characteristically includes steps of reacting, for deprotection, an amino acid compound protected with an Fmoc group with an amine compound containing a nitrogen atom which is bonded to at least one hydrogen atom to give a reaction mixture, contacting the mixture with carbon dioxide, and removing the resulting carbonate of the dibenzofulvene amine adduct. In addition, a method including reacting, for deprotection, an amino acid compound protected with an Fmoc group with DBU and the like, wherein a nitrogen atom does not contain a hydrogen atom, adding an amine compound containing a nitrogen atom which is bonded to at least one hydrogen atom during or after the reaction to the obtained reaction mixture to afford a dibenzofulvene amine adduct, contacting the adduct with carbon dioxide to give carbonate of the dibenzofulvene amine adduct, and removing the carbonate may also be employed.

By such operations, the deprotected amino acid compound is surprisingly dissolved in an organic solvent, and the carbonate of the dibenzofulvene amine adduct can be handled as a solid since it hardly dissolves in an organic solvent. As a result, the dibenzofulvene amine adduct can be removed by separating according to a convenient solid-liquid separation means such as filtration and the like. Therefore, a desired amino acid compound can be conveniently purified or isolated without performing an operation such as crystallization, chromatography and the like.

Dibenzofulvene is a by-product resulting from the removal of an Fmoc group, and a dibenzofulvene amine adduct means a compound wherein a nitrogen atom which is bonded to at least one hydrogen atom of an amine compound is added to dibenzofulvene.

The "amino acid compound" of the "amino acid compound protected with an Fmoc group" is a compound having a primary amino group and/or a secondary amino group, as well as a carboxyl group and/or an esterified, thioesterified or amidated carboxyl group, in a molecule. Preferable examples of such amino acid compound include peptide (including those wherein the C-terminal is amidated or esterified), amino acid ester, amino acid amide and the like.

Here, the peptide, amino acid ester and amino acid amide may have, besides the primary amino group or secondary amino group as the N-terminal, an amine side chain functional group (amino group, indole, guanidine etc.), and these amine side chain functional groups may be protected with a protecting group. Also, the carboxyl group and amide group at the C-terminal of peptide may or may not be protected. Furthermore, when the peptide, amino acid ester and amino acid amide have a side chain functional group other than a carboxyl group, an amide group and an amino group, the side chain functional group may or may not be protected.

When the carboxyl group is protected, preferable examples of the carboxyl-protecting group include alkyl having 1 to 6 carbon atoms such as methyl, ethyl, tert-butyl and the like, benzyl, p-nitrobenzyl, p-methoxybenzyl, Dpm, allyl, Bpr and the like.

When the amide group is protected, preferable amide-protecting groups include Dmb, bis(4-methoxyphenyl)methyl and the like.

In the "amino acid compound protected with an Fmoc group", at least one of a primary amino group and/or a secondary amino group and an amine side chain functional group that the amino acid compound has only need to be protected with the Fmoc group. The primary amino group and/or the secondary amino group, and the amine side chain functional group, which are not protected with an Fmoc group, may be unprotected, or may be protected with a protecting group for an amino group (amine-protecting group) (e.g., Boc, Z, Bsmoc, Alloc, Ac etc.) other than the Fmoc group.

As the "amino acid compound protected with an Fmoc group", preferred is a compound wherein the N-terminal amino group is protected with an Fmoc group and, when an amine side chain functional group is present, the amine side chain functional group is protected with an amino-protecting group other than the Fmoc group.

The "amine compound containing a nitrogen atom which is bonded to at least one hydrogen atom" is not particularly limited as long as it has nucleophilicity of the level sufficient to remove an Fmoc group, and the nitrogen atom having at least one hydrogen atom forms an adduct with dibenzofulvene. Examples thereof include monoamines (e.g., diethylamine, dimethylamine, pyrrolidine, piperidine, morpholine, propylamine etc.), polyvalent amines (diamines such as 4-aminomethylpiperidine, 4-dimethylaminopiperidine, 1,5-diaminopentane, 1,8-diaminooctane, N,N'-dimethyl-1,6-diaminohexane, N,N-diethylethylenediamine, aminomethylpyridine, 1,2-diaminocyclohexane and the like, triamines such as diethylenetriamine and the like).

The amine compound containing a nitrogen atom which is bonded to at least one hydrogen atom is preferably a polyvalent amine, particularly preferably 4-aminomethylpiperidine, 4-dimethylaminopiperidine, 1,5-diaminopentane, 1,2-diaminocyclohexane, diethylenetriamine and the like, since a dibenzofulvene amine adduct thereof forms carbonate well, and the carbonate shows good crystallinity in a solvent.

The "removal of dibenzofulvene-amine" means removal of dibenzofulvene-amine from a reaction mixture containing N-unprotected amino acid compound obtained by deprotection and the dibenzofulvene-amine, and includes removal of a dibenzofulvene amine adduct.

The first embodiment of the method for removal of dibenzofulvene-amine of the present invention can be performed by (a) a step of mixing an amino acid compound protected with an Fmoc group with an amine compound containing a nitrogen atom which is bonded to at least one hydrogen atom in an organic solvent to give a reaction mixture containing the amino acid compound and a dibenzofulvene amine adduct, (b) a step of contacting the reaction mixture with carbon dioxide to convert the dibenzofulvene amine adduct to carbonate, and (c) a step of removing the carbonate of the dibenzofulvene amine adduct from the reaction mixture.

In addition, the second embodiment of the method for removal of dibenzofulvene amine of the present invention can be performed by (a') a step of mixing an amino acid compound protected with an Fmoc group with an amine compound containing a nitrogen atom which is not bonded to a hydrogen atom in an organic solvent to give a reaction mixture containing the amino acid compound and dibenzofulvene, (b') a step of mixing the reaction mixture during the reaction of step (a') or after completion of the reaction with an amine compound containing a nitrogen atom which is bonded to at least one hydrogen atom in an organic solvent to give a reaction mixture containing the amino acid compound and a dibenzofulvene amine adduct, (c') a step of contacting the reaction mixture with carbon dioxide to convert the dibenzofulvene amine adduct to carbonate, and (d') a step of removing the carbonate of the dibenzofulvene amine adduct from the reaction mixture.

The amount of the amine compound containing a nitrogen atom which is bonded to at least one hydrogen atom to be used is generally 2 to 100 equivalents, preferably 5 to 20 equivalents, relative to the amino acid compound protected with an Fmoc group. When the amount is lower than this range, the unreacted amino acid compound protected with an Fmoc group tends to remain, and when the amount is high, removal of excess amine compound tends to be difficult.

The solvent for the deprotection reaction in step (a) may be any as long as it does not inhibit the deprotection reaction, and depending on the amino acid compound protected with an Fmoc group, which is the target of deprotection, and examples thereof include DMF, N-methylpyrrolidone (NMP), ethyl acetate, acetonitrile, tetrahydrofuran (THF), chloroform and the like and a mixed solvent thereof. When a mixed solvent is used, the solvents can be mixed at any ratio. The amount of the solvent to be used is generally 3- to 100-fold weight, preferably 5- to 20-fold weight, relative to the amino acid compound protected with an Fmoc group.

While the reaction temperature in step (a) varies depending on the amino acid compound protected with an Fmoc group, which is the target of deprotection, it is generally within the range of 0 to 40° C., preferably 5 to 30° C. The reaction time is generally 1 to 20 hr when the temperature is within the above-mentioned range.

Step (a') can be performed in the same manner as in step (a) and using the "amine compound containing a nitrogen atom which is not bonded to a hydrogen atom" instead of the "amine compound containing a nitrogen atom which is bonded to at least one hydrogen atom".

Examples of the "amine compound containing a nitrogen atom which is not bonded to a hydrogen atom" include DBU and the like.

Step (b') can be performed by adding an amine compound containing a nitrogen atom which is bonded to at least one hydrogen atom to the reaction mixture during the reaction of step (a') or after completion of the reaction, and stirring the mixture. The amount of use of the amine compound containing a nitrogen atom which is bonded to at least one hydrogen atom, and other conditions are the same as those in step (a).

After completion of the reaction of step (a) or step (b'), carbon dioxide is contacted with the reaction mixture containing the obtained amino acid compound and dibenzofulvene amine adduct.

The method of contacting carbon dioxide is not particularly limited, and examples thereof include a method of blowing carbon dioxide gas through a tube, a method of adding carbonated water, a method of adding dry ice and the like. From the aspect of operability, a method of blowing carbon dioxide gas through a tube is preferable.

When the deprotection of step (a) is performed in a solvent (e.g., DMF, NMP) that easily dissolves carbonate of the dibenzofulvene amine adduct, a solvent that hardly dissolves carbonate of dibenzofulvene amine adduct is preferably added to the reaction mixture, and the mixture is contacted with carbon dioxide. Examples of such solvent include ethyl acetate, chloroform, methylene chloride, tetrahydrofuran, acetonitrile, acetone, ether and the like. While the amount of the solvent to be used is not particularly limited, it may be selected from the range of 5- to 50-fold volume relative to the solvent used for the deprotection.

The reaction temperature of step (b) is generally within the range of 0 to 40° C., preferably 5 to 30° C. The reaction time is generally 5 min to 1 hr within the range of the above-mentioned temperature.

After completion of step (b), a mixture wherein an amino acid compound is dissolved in a solvent and carbonate of a dibenzofulvene amine adduct is precipitated can be obtained, and the dibenzofulvene amine adduct can be removed by removing the carbonate from the mixture by a general solid-liquid separation method.

As the solid-liquid separation method, a general method such as filtration, centrifugation, decantation and the like can be adopted without limitation. From the aspect of operability, filtration is preferable.

The solution (filtrate) containing the amino acid compound obtained by step (c) allows removal of the carbonate of the dibenzofulvene amine adduct remaining in a small amount, excess amine compound, water-soluble solvent such as DMF etc., and the like by washing with water, washing with a basic or acidic aqueous solution and the like as necessary.

An amino acid compound after deprotection of an Fmoc group can be isolated by concentrating the thus-obtained solution. The solution of the amino acid compound can also be used directly as a starting material of the below-mentioned liquid phase peptide synthesis method.

Where necessary, moreover, the amino acid compound may be isolated as an acid addition salt (hydrochloride, toluenesulfonate, methanesulfonate, hydrobromide, trifluoroacetate etc.) by adding an acid (hydrogen chloride, toluenesulfonic acid, methanesulfonic acid, hydrobromic acid, trifluoroacetic acid etc.) to the solution as necessary.

Steps (c') and (d') can be performed in the same manner as steps (b) and (c), respectively.

2. Liquid Phase Peptide Synthesis Method

When the amino acid compound is peptide, an amino acid ester or amino acid amide, the method for removal of dibenzofulvene amine of the present invention can be preferably applied to a liquid phase peptide synthesis method. An embodiment wherein the method for removal of dibenzofulvene amine of the present invention is applied to a liquid phase peptide synthesis method (hereinafter to be referred to as the "liquid phase peptide synthesis method of the present invention" in the present specification) is explained in the following. Needless to say, the present invention is not limited thereto.

2-1. Explanation of Terms

The meanings of the terms used for the liquid phase peptide synthesis method of the present invention are now explained.

The "peptide" in the liquid phase peptide synthesis method of the present invention includes both cases that the C-terminal is a carboxyl group or an amide group.

In the liquid phase peptide synthesis method of the present invention, the deprotection of the "peptide, amino acid ester or amino acid amide protected with an Fmoc group" is not particularly limited as long as it is a deprotection of an Fmoc group included in the liquid phase peptide synthesis method. For example, it may be N-terminal deprotection step as described below or a deprotection of a side chain amino group in the final deprotection. It is preferably a deprotection to produce an amino group to be the object of coupling in the next step in the peptide elongation reaction to be described below.

When an amino acid is shown by "H-AA-OH" in the liquid phase peptide synthesis method of the present invention, it means that the left side is an amino group, the right side is a carboxyl group, and each of the amino group and the carboxyl group is not protected.

In this case, for example, when the carboxyl group is protected, it is shown by "H-AA-$OPG_0$", and when the amino group is protected, it is shown by "$PG_n$-AA-OH".

When the carboxyl group of amino acid with a protected amino group becomes active ester, the amino acid is shown by "$PG_n$-AA-OE".

A symmetric acid anhydride of $PG_n$-AA-OH is shown by "$(PG_n$-AA$)_2$-O".

In the liquid phase peptide synthesis method of the present invention, when amino acid amide is shown by "H-AA-$NH_2$", it means that the left side is an amino group, the right side is an amide group, and each of the amino group and amide group is not protected.

In this case, for example, when the amide group is protected, it is shown by "H-AA-$NHPG_0$", and when the amino group is protected, it is shown by "$PG_n$-AA-$NH_2$".

When amino acid or amino acid amide has a protected side chain functional group, it is shown by "H-AA(PG)-(OH or $NH_2$)" (PG is a protecting group of the side chain functional group).

When peptide is shown by "H-$AA_{n'}$-$AA_{n'-1}$- .... -$AA_1$-(OH or $NH_2$)" (subscript n' is any integer of two or above) in the liquid phase peptide synthesis method of the present invention, it means that the left side is N-terminal, the right side is C-terminal, and the peptide contains amino acid residues in the number of n' with unprotected N-terminal and unprotected C-terminal. Here, the N-terminal is not limited to an α-amino group of the amino acid residue, and also includes a side chain amino group (e.g., an ε-amino group of Lys) when peptide elongation is performed via the side chain amino group, hereinafter the same.

In this case, for example, when the C-terminal is protected, it is shown by "H-$AA_{n'}$-$AA_{n'-1}$- .... -$AA_1$-($OPG_0$ or $NHPG_0$)", and further, when the N-terminal is protected, it is shown by "$PG_n$-$AA_{n'}$-$AA_{n'-1}$- .... -$AA_1$-($OPG_0$ or $NHPG_0$)".

The amino acid residue to be a constituent unit of peptide synthesized by the liquid phase peptide synthesis method of the present invention nonlimitatively includes natural amino acids and nonnatural amino acids, as well as L forms, D forms and racemates thereof.

Examples of the natural amino acid include Gly, Ala, Val, Leu, Ile, Ser, Thr, Asn, Gln, Asp, Glu, Lys, Arg, Cys, Met, Phe, Tyr, Trp, His, Pro, Orn, Sar, β-Ala, GABA and the like, or amide forms thereof.

Examples of the nonnatural amino acid include Dap and the like.

In addition, when the amino acid has a functional group in the side chain, the functional group may be protected with a protecting group. Examples of such side chain-protected amino acid include γ-Bzl-Glu or β-Bzl-Asp, wherein a carboxyl group at the γ-position of Glu or β-position of Asp is protected with a benzyl group; γ-tBu-Glu or β-tBu-Asp, wherein a carboxyl group at the γ-position of Glu or β-position of Asp is protected with a tert-butyl group; ε-Z-Lys, ε-Boc-Lys or ε-iPr-ε-Boc-Lys, wherein an amino group at the ε-position of Lys is protected; S-phenylcarbamoyl-Cys wherein an SH group of Cys is protected with a phenylcarbamoyl group; S-Trt-Cys wherein an SH group of Cys is protected with a trityl group; a derivative wherein a hydroxyl group of Tyr, Thr and Ser is protected with Bzl; a derivative wherein a hydroxyl group of Tyr, Thr and Ser is protected with tBu; a derivative wherein a guanidyl group of Arg is protected with Pbf and the like.

In the liquid phase peptide synthesis method of the present invention, the "N-protected amino acid" means an amino acid wherein the amino group is protected and the carboxyl group is unprotected, which is shown by "$PG_n$-AA-OH" according to the above-mentioned notation.

In the liquid phase peptide synthesis method of the present invention, the "N-protected amino acid amide" means an amino acid amide wherein the amino group is protected and an amide group is unprotected, and according to the above-mentioned notation, it is shown by "$PG_n$-AA-$NH_2$".

In the liquid phase peptide synthesis method of the present invention, the "N-protected amino acid activated ester" means an amino acid wherein the amino group is protected and the carboxyl group becomes active ester with E, and according to the above-mentioned notation, it is shown by "$PG_n$-AA-OE".

In the N-protected amino acid activated ester that can be isolated, E is pentafluorophenyl, Su or Nb, and other N-protected amino acid activated esters are produced in a reaction system by reacting N-protected amino acid with a condensing agent (e.g., EDC) and an activator (e.g., HOBt).

In the liquid phase peptide synthesis method of the present invention, the "N-Fmoc amino acid" means an amino acid residue wherein the amino group is protected with Fmoc, and the carboxyl group is unprotected, which is shown by "Fmoc-AA-OH" according to the above-mentioned notation.

In the liquid phase peptide synthesis method of the present invention, the "N-Fmoc amino acid amide" means an amino acid residue wherein the amino group is protected with Fmoc, and the amide group is unprotected, and according to the above-mentioned notation, it is shown by "Fmoc-AA-$NH_2$".

In the liquid phase peptide synthesis method of the present invention, the "N-Fmoc amino acid activated ester" means an amino acid residue wherein an amino group is protected with Fmoc and a carboxyl group becomes active ester with E, and according to the above-mentioned notation, it is shown by "Fmoc-AA-OE".

In the N-Fmoc amino acid activated ester that can be isolated, E is pentafluorophenyl, Su or Nb. Other N-Fmoc amino acid activated esters are produced in a reaction system by reacting N-Fmoc amino acid with a condensing agent (e.g., EDC) and an activator (e.g., HOBt).

In the liquid phase peptide synthesis method of the present invention, the "C-protected peptide" means a peptide containing amino acid residues in any number, wherein the C-terminal is protected and the N-terminal is not protected. According to the above-mentioned notation, it is shown by "H-$AA_{n'}$-$AA_{n'-1}$- . . . -$AA_1$($OPG_0$ or $NHPG_0$)" (n' is an integer of two or above).

In the present invention, the "C-protected amino acid" means an amino acid wherein the carboxyl group is protected and the amino group is not protected. According to the above-mentioned notation, it is shown by "H-AA-$OPG_0$".

The "C-protected amino acid amide" in the present invention means an amino acid wherein the amide group is protected and the amino group is not protected. According to the above-mentioned notation, it is shown by "H-AA-$NHPG_0$".

In the liquid phase peptide synthesis method of the present invention, the "N,C-diprotected peptide" means a peptide containing amino acid residues in any number, wherein both the N-terminal and the C-terminal are protected. According to the above-mentioned notation, it is shown by "$PG_n$-$AA_{n'}$-$AA_{n'-1}$- . . . -$AA_1$-($OPG_0$ or $NHPG_0$)" (n' is an integer of two or above). In addition, for example, N,C-diprotected peptide wherein the N-terminal is protected with Fmoc and the C-terminal is protected, is shown by "N-Fmoc-C-protected peptide".

In the liquid phase peptide synthesis method of the present invention, the "intermediate peptide" means a synthetic intermediate peptide obtained in each step in the liquid phase peptide synthesis, which contains amino acid residues in a number less than that in the final object peptide. Preferable intermediate peptide is C-protected peptide obtained after deprotection of N-terminal as mentioned below.

In the liquid phase peptide synthesis method of the present invention, examples of the "condensing agent" include DCC, EDC (including hydrochloride and free form), DIPC, BOP, PyBOP, PyBroP, HBTU, HCTU, TBTU, HATU, CDI, DMT-MM and the like.

In the liquid phase peptide synthesis method of the present invention, the "activator" is a reagent that leads a carboxyl group to activated ester, symmetric acid anhydride and the like in the co-presence of a condensing agent, and facilitates amide bond formation. It is shown by "HOE". Specific examples include HOBt, HOCt, HOAt, HOOBt, HOSu, HOPht, HONB, pentafluorophenol and the like.

In the liquid phase peptide synthesis method of the present invention, the "one-pot synthesis" means, in the liquid phase peptide synthesis method, synthesis up to objective peptide without taking out an intermediate peptide obtained in each step from the reaction vessel.

2-2. Liquid Phase Peptide Synthesis Method

The peptide finally synthesized by the liquid phase peptide synthesis method of the present invention is not particularly limited, and can be preferably utilized for the synthesis of synthetic pharmaceutical peptide, cosmetic, electronic material (organic EL etc.), food and the like.

While the number of the constituent amino acid residues of the peptide is not particularly limited, it is preferably about 2 to 20 residues found in general synthetic peptide.

In addition, the liquid phase peptide synthesis method of the present invention is suitable for the liquid phase peptide synthesis method and the like using C-protected peptide (e.g., peptide including ε-Boc-Lys, S-tBu-Cys etc.) wherein amino acid side chain functional group and/or C-terminal protecting group is protected with a protecting group which is removed with an acid.

The "liquid phase peptide synthesis method" means that it is not a solid phase method, and the method of the present invention includes not only a case where all reagents are dissolved in a solvent, but also what is called a heterogeneous reaction where reagents are entirely or partly undissolved but suspended and the like in a solvent.

For the liquid phase peptide synthesis method, a general method conventionally used in the peptide synthesis chemistry can be employed without particular limitation.

Specifically, it is a method shown in the following scheme, in other words, a method including repeats of one cycle reaction (hereinafter to be referred to as "peptide elongation reaction" in the present specification) consisting of a step of obtaining N,C-diprotected peptide ($PP_{n+1}$) wherein one amino acid residue is elongated by (1) condensing C-protected peptide ($P_n$,) wherein n' is any integer of two or above, and means that peptide contains amino acid residues in the number of n', hereinafter the same) or, in the first peptide elongation, C-protected amino acid or C-protected amino acid amide ($A_1$) (hereinafter to be collectively referred to as "C-protected peptide ($P_n$) or the other" (n is any integer of one or more and, when n is 1, it means C-protected amino acid or C-protected amino acid amide ($A_1$), hereinafter the same) in the present specification) with N-protected amino acid ($PA_{n+1}$) in the presence of a condensing agent (and preferably an activator), or (2) condensing C-protected peptide ($P_n$) or the other with N-protected amino acid activated ester ($PAE_{n+1}$) (hereinafter to be referred to as "coupling step (1)" and "coupling step (2)", respectively, in the present specification), and a step of obtaining C-protected peptide ($P_{n+1}$) by removing an amino-protecting group of the obtained N,C-diprotected peptide ($PP_{n+1}$) (hereinafter to be referred to as "N-terminal deprotection step" in the present specification). In the final step, the object peptide (P) can be obtained by removing the carboxy-protecting group or amide-protecting group of C-protected peptide ($P_m$) and a protecting group in case of a protected side chain functional group (hereinafter to be is referred to as the "final deprotection step" in the present specification).

In the peptide synthesis method in the present invention, the nth peptide elongation reaction is indicated as "peptide elongation reaction (n)", and respective steps constituting the peptide elongation reaction (n) are indicated as "coupling step (1-n)", "coupling step (2-n)" and "N-terminal deprotection step (n)".

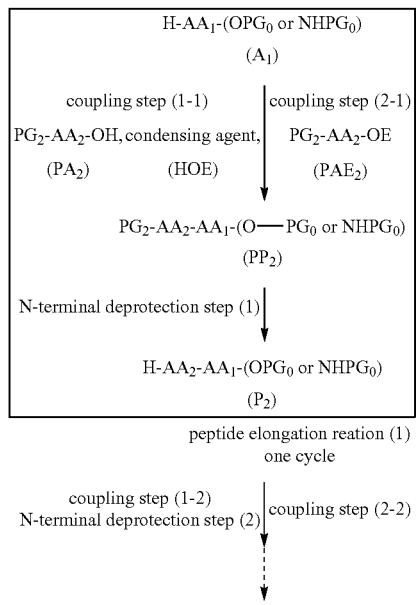

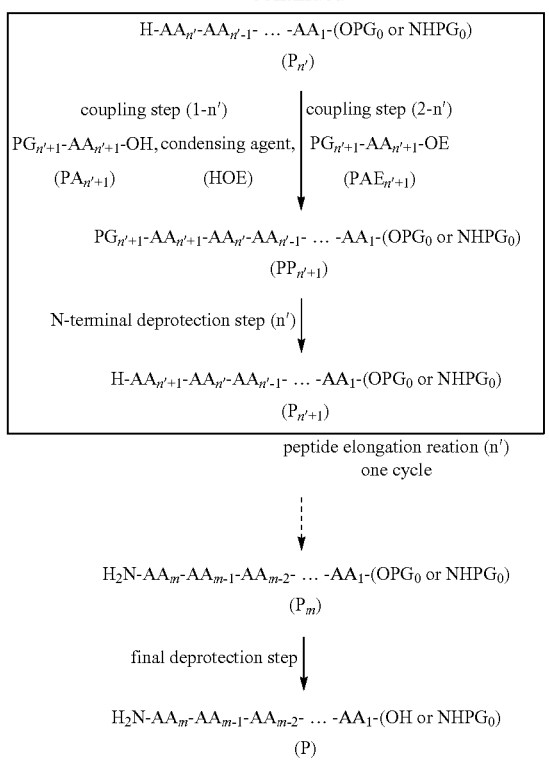

wherein m is the number of amino acid residues of the objective peptide, and other symbols are as defined above.

The liquid phase peptide synthesis method of the present invention is characterized in that coupling step (1) is performed by using N-Fmoc amino acid, or coupling step (2) is performed by using N-Fmoc amino acid activated ester by at least once of a series of peptide elongation reactions to give N-Fmoc-C-protected peptide and, in an N-terminal deprotection step, the N-Fmoc-C-protected peptide is subjected to the method for removal of dibenzofulvene of the present invention, wherein, for example, in the first embodiment, deprotection by reaction with an amine compound containing a nitrogen atom which is bonded to at least one hydrogen atom gives a mixture containing C-protected peptide ($P_{n+1}$) and a dibenzofulvene amine adduct, the mixture is contacted in the subsequent workup with carbon dioxide to convert the dibenzofulvene amine adduct to carbonate, and the carbonate is removed (hereinafter to be referred to as "the peptide elongation reaction of the present invention", and peptide elongation reaction of the nth time is shown as "the peptide elongation reaction (n) of the present invention"). While the application of the first embodiment of the removal method of dibenzofulvene of the present invention is explained below, it is needless to say that the second embodiment can also be performed in the same manner.

In the liquid phase peptide synthesis method of the present invention, the peptide elongation reaction of the present invention only needs to be included at least once. However, all steps are preferably performed in the peptide elongation reaction of the present invention, whereby the objective peptide can be synthesized in one-pot.

The scheme of the peptide elongation reaction (n) of the present invention is shown below.

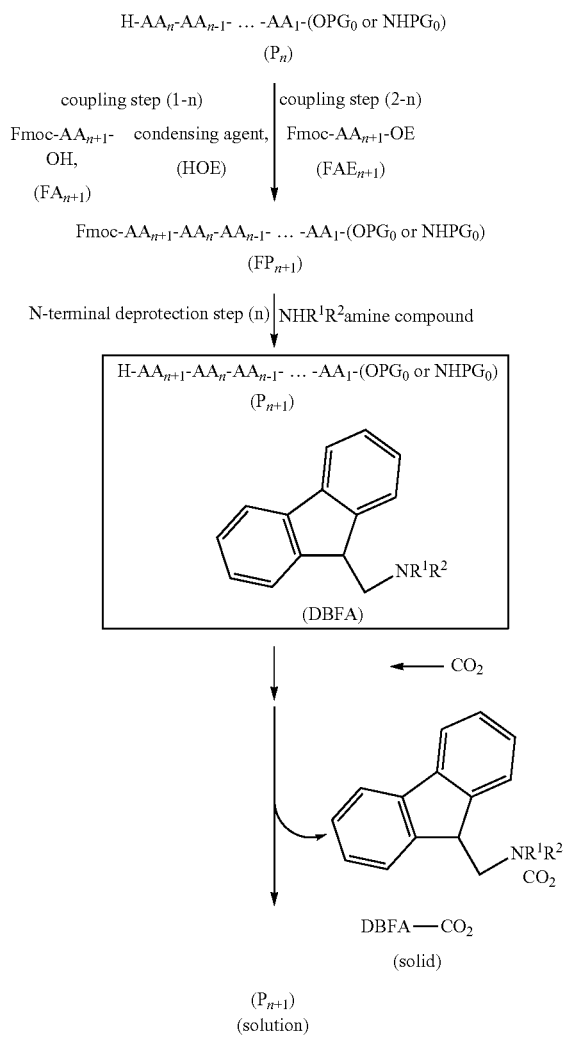

wherein DBFA is a dibenzofulvene amine adduct, DBFA-$CO_2$ is carbonate of the dibenzofulvene amine adduct, $HNR^1R^2$ corresponds to an amine compound used for deprotection (in case of secondary amine), and other symbols are as defined above.

By contacting a mixture containing C-protected peptide ($P_{n+1}$) and a dibenzofulvene amine adduct with carbon dioxide, most of the dibenzofulvene amine adduct carbonate is unexpectedly precipitated as a solid, whereby the dibenzofulvene amine adduct can be removed by a convenient means such as filtration and the like. Thus, the obtained C-protected peptide ($P_{n+1}$) can be provided to the next peptide elongation reaction (n+1) without an isolation and purification operation such as crystallization, chromatography and the like, thus leading to the one-pot synthesis.

The liquid phase peptide synthesis method of the present invention is explained in detail in the following.

2-2-1. Coupling Step (1)

In coupling step (1) in the peptide elongation reaction of the present invention, for example, N-Fmoc amino acid ($FA_{n+1}$), C-protected peptide ($P_n$) or the other, and a condensing agent are mixed (preferably with an activator) in a solvent to give N-Fmoc-C-protected peptide ($FP_{n+1}$) wherein one amino acid residue is elongated. While the order of addition is not particularly limited, when the C-protected peptide ($P_n$) or the other is obtained by peptide elongation reaction (n−1) before this one, N-Fmoc amino acid ($FA_{n+1}$) and a condensing agent can be added to a solution of the C-protected peptide ($P_n$) or the other in a reaction vessel.

The amount of N-Fmoc amino acid ($FA_{n+1}$) to be used is generally 0.9 to 4.0 equivalents, preferably 1.0 to 1.5 equivalents, relative to the C-protected peptide ($P_n$) or the other. When the amount is smaller than this range, unreacted C-protected peptide ($P_n$) or the other tends to remain, and when the amount is higher, excess N-Fmoc amino acid ($FA_{n+1}$) cannot be removed easily.

When C-protected peptide ($P_n$) or the other is used as acid addition salt, a base is added for neutralization. Examples of the base include triethylamine, diisopropylethylamine, pyridine, N-methylmorpholine and the like. The amount of the base to be used is generally 0.5 to 2.0 equivalents, preferably 1.0 to 1.5 equivalents, relative to the C-protected peptide ($P_n$) or the other. When the amount of the base to be used is smaller than this range, neutralization becomes insufficient and the reaction does not proceed smoothly.

As the condensing agent, those exemplified above can be used without particularly limitation. Examples thereof include EDC (free form or hydrochloride), DIPC, DCC, PyBOP, HBTU, HCTU and DMT-MM. EDC is preferable since the residual condensing agent and decomposed condensing agent can be removed with ease by washing. The amount of the condensing agent to be used is generally 0.8 to 4.0 equivalents, preferably 1.0 to 1.5 equivalents, relative to N-Fmoc amino acid ($FA_{n+1}$).

In coupling step (1), an activator is preferably added to promote the reaction and suppress side reactions such as racemization and the like. When an activator is present, activated ester of N-protected amino acid, and the like are temporarily produced in the reaction system.

As the activator, those exemplified above can be used without particularly limitation, and HOBt, HOOBt, HOCt, HOAt, HONb, HOSu and the like are preferable. The amount of the activator to be used is generally 0 to 4.0 equivalents, preferably 0.1 to 1.5 equivalents, relative to N-Fmoc amino acid ($FA_{n+1}$).

The solvent may be any as long as it does not inhibit the reaction, and examples thereof include N,N-dimethylformamide (DMF), N-methylpyrrolidone (NMP), ethyl acetate, tetrahydrofuran (THF), acetonitrile, chloroform, methylene chloride and the like or a mixed solvent thereof, with preference given to ethyl acetate and DMF. The amount of the solvent to be used is generally 3- to 100-fold weight, preferably 5- to 20-fold weight, relative to the C-protected peptide ($P_n$) or the other.

The reaction temperature is generally within the range of −20° C. to 40° C., preferably 0° C. to 30° C. The reaction time is generally 0.5 to 30 hr within the above-mentioned temperature range.

Since the workup after completion of coupling step (1) reaction is the same as for coupling step (2), it is explained all together in the below-mentioned 2-2-3.

2-2-2. Coupling Step (2)

In coupling step (2) in the peptide elongation reaction of the present invention, for example, N-Fmoc amino acid activated ester ($FAE_{n+1}$) and the C-protected peptide ($P_n$) or the other are mixed in a solvent to give N-Fmoc-C-protected peptide ($FP_{n+1}$). While the order of addition is not particularly limited, when the C-protected peptide ($P_n$) or the other is obtained by peptide elongation reaction (n−1) before this one, N-Fmoc amino acid activated ester ($FAE_{n+1}$) can be added to a solution of C-protected peptide ($P_n$) or the other in a reaction vessel.

The amount of N-Fmoc amino acid activated ester ($FAE_{n+1}$) to be used is the same as N-Fmoc amino acid ($FA_{n+1}$) in coupling step (1).

In addition, other reaction conditions such as base, solvent and amounts thereof to be used, reaction temperature, reaction time and the like are the same as those for coupling step (1).

2-2-3. Workup of Coupling Steps (1) and (2)

After the completion of the reactions of coupling steps (1) and (2), solid nucleophile removing reagents such as mercapto group-supported silica gel and the like (e.g., SH silica (manufactured by Fuji Silysia Chemical Ltd.) etc.) may be added, and the mixture is stirred and filtered to remove residues and byproducts in the reaction mixture that can be condensed with amine components, such as N-Fmoc amino acid activated ester ($FAE_{n+1}$), isourea ester of N-Fmoc amino acid, symmetric acid anhydride of N-Fmoc amino acid and the like. In addition, activated ester may be positively deactivated in the washing step by washing with weak alkaline aqueous solution such as sodium carbonate and the like.

In the workup in coupling steps (1) and (2), washing with acidic aqueous solution and/or washing with basic aqueous solution is preferably performed. The washing with acidic aqueous solution can remove C-protected peptide, residual condensing agent and a decomposed product thereof, a base and the like into the aqueous layer. The washing with basic aqueous solution can remove additive, residual N-Fmoc amino acid and the like into the aqueous layer.

The washing with acidic aqueous solution is performed by, for example, stirring the reaction mixture with dilute aqueous hydrochloric acid solution (e.g., 1N aqueous hydrochloric acid solution), or an aqueous solution of sulfuric acid, formic acid, citric acid, phosphoric acid and the like, partitioning and removing the aqueous layer.

The washing with basic aqueous solution is performed by, for example, stirring the reaction mixture with an aqueous solution such as aqueous sodium hydrogen carbonate solution (e.g., 5% aqueous sodium hydrogen carbonate solution), aqueous sodium carbonate solution, aqueous potassium carbonate solution and the like, partitioning and removing the aqueous layer.

N-Fmoc-C-protected peptide ($FP_{n+1}$) can be obtained by further washing with water as necessary and concentrating the organic layer, which can be subjected to the N-terminal deprotection step without taking out from the vessel. In addition, it may be used without concentration for the N-terminal deprotection step as a solution of N-Fmoc-C-protected peptide ($FP_{n+1}$).

When the liquid phase peptide synthesis method of the present invention includes a coupling step using an amine-protecting group other than Fmoc, it can also be performed in the same manner as in the above.

2-2-4. N-Terminal Deprotection Step

In the N-terminal deprotection step of the peptide elongation reaction of the present invention, C-protected peptide ($P_{n+1}$) can be obtained by reacting N-Fmoc-C-protected peptide ($FP_{n+1}$) with an amine compound (including an amine compound containing a nitrogen atom which is bonded to at least one hydrogen atom and an amine compound containing a nitrogen atom which is not bonded to a hydrogen atom) in a solvent. Specifically, the amine can be added to a solution of N-Fmoc-C-protected peptide ($FP_{n+1}$) obtained in the coupling step.

By subjecting the reaction mixture obtained by the deprotection to the removal method of dibenzofulvene of the present invention, for example, by contacting a mixture of C-protected peptide ($P_{n+1}$) and a dibenzofulvene amine adduct with carbon dioxide to allow precipitation of carbonate of the dibenzofulvene amine adduct and filtering same, the dibenzofulvene amine adduct can be removed.

When the elongation reaction is started, C-protected peptide ($P_n$) and the like become C-protected amino acid or C-protected amino acid amide. The C-protected amino acid and C-protected amino acid amide can be prepared as follows. That is, a carboxyl group of N-Fmoc amino acid is esterified or amidated according to a conventional method to give N-Fmoc-C-protected amino acid or N-Fmoc-C-protected amino acid amide. In the same manner as above, the obtained N-Fmoc-C-protected amino acid or N-Fmoc-C-protected amino acid amide is reacted with an amine compound in a solvent to give C-protected amino acid (amino acid ester) or C-protected amino acid amide (amino acid amide). In the same manner as above, a mixture of C-protected amino acid or C-protected amino acid amide and a dibenzofulvene amine adduct, which is obtained by the deprotection, is contacted with carbon dioxide to allow precipitation of carbonate of the dibenzofulvene amine adduct, and the mixture is filtered to remove the dibenzofulvene amine adduct. Removal of an Fmoc group of such N-Fmoc-C-protected amino acid or N-Fmoc-C-protected amino acid amide is also included in the N terminal deprotection step mentioned here.

The N-terminal deprotection step in the liquid phase peptide synthesis method of the present invention can be performed in the same manner by replacing, in the "method for removal of dibenzofulvene-amine" of the above-mentioned 1, the "amino acid compound protected with an Fmoc group" with "N-Fmoc-C-protected peptide ($FP_{n+1}$)", "N-Fmoc-C-protected amino acid" or "N-Fmoc-C-protected amino acid amide", and the "amino acid compound" with "C-protected peptide ($P_{n+1}$)", "C-protected amino acid" or "C-protected amino acid amide".

The solution of C-protected peptide ($P_{n+1}$) isolated in the N-terminal deprotection step can be directly used with or without concentration for the next peptide elongation reaction.

When the peptide synthesis in the present invention includes an N-terminal deprotection step using an N-terminal protecting group other than Fmoc, it can be performed according to a general N-terminal deprotection method according to the kind of the amino-protecting group conventionally used for the peptide synthesis chemistry.

As mentioned above, according to the method of the present invention, a dibenzofulvene amine adduct can be conveniently removed from the reaction mixture obtained by reacting an amino acid compound protected with an Fmoc group with an amine compound for deprotection in the N-terminal deprotection step. Therefore, the next condensation step, i.e., the next peptide elongation reaction, in the liquid phase peptide synthesis method can be performed without taking intermediate peptide from the reaction vessel. In other words, the next condensation step can be performed without isolating the obtained intermediate peptide as a solid by crystallization and the like. Thus, according to the method of the present invention, the object final peptide can be synthesized in one-pot by the liquid phase peptide synthesis method.

2-2-5. Final Deprotection Step

In the peptide synthesis in the present invention, the objective peptide (P) can be obtained by removing $PG_0$ and side chain protecting group from C-protected peptide ($P_m$) constructed up to the objective peptide.

For the final deprotection step, a deprotection method known per se can be employed without particular limitation according to the kind of $PG_0$ or side chain protecting group.

For example, in the case of a lower alkyl group such as Me, Et and the like, the reaction can be performed with a base such as sodium hydroxide, potassium hydroxide and the like in a solvent such as water, aqueous organic solvent and the like at −20° C. to 40° C. for 0.5 to 10 hr.

tBu, Pbf, Dmb, bis(4-methoxyphenyl)methyl and the like can be removed by reaction with an acid such as trifluoroacetic acid, hydrochloric acid, methanesulfonic acid, tosylic acid, formic acid and the like in a solvent such as chloroform, methylene chloride, ethyl acetate, dioxane and the like at −20° C. to 40° C. for 0.5 to 10 hr.

Z can be removed by hydrogenation reaction using a catalyst such as palladium carbon and the like in a solvent such as methanol, DMF, acetic acid and the like at 0° C. to 40° C. for 0.5 to 100 hr, or by reaction with a strong acid such as hydrogen fluoride, trifluoromethanesulfonic acid and the like at −20° C. to 40° C. for 0.5 to 10 hr.

In the case of an alloc group, the reaction can be performed with a homogeneous zero-valent palladium catalyst such as tetrakistriphenylphosphine palladium and the like. The homogeneous zero-valent palladium catalyst is used in 0.01 to 1.0 equivalent, preferably 0.05 to 0.5 equivalent.

When the side chain amino group protected with an Fmoc group is deprotected in the final deprotection step, the method for removal of dibenzofulvene amine of the present invention can also be applied in the workup in the same manner as in the N-terminal deprotection step.

Peptide (P) synthesized by the method of the present invention can be isolated and purified by a method conventionally used in the peptide chemistry. For example, peptide (P) can be isolated and purified by extraction and washing, crystallization, chromatography and the like of the reaction mixture in the workup of the C-terminal deprotection step.

Other features of the invention will become apparent in the course of the following descriptions of exemplary embodiments which are given for illustration of the invention and are not intended to be limiting thereof.

EXAMPLES

Example 1

Synthesis of peptide acid using diphenylmethyl (Dpm) group

Synthesis of fibronectin active fragment (Gly-Arg-Gly-Asp-Ser)

(1) Fmoc-Ser(tBu)-ODpm

To a solution of benzophenone hydrazone (37.5 g, 0.191 mol) in methylene chloride (450 ml) were added anhydrous magnesium sulfate (33.0 g) and manganese dioxide (75.0 g, 0.863 mol), and the mixture was stirred at room temperature for 2 hr. The insoluble material was filtered off, and the filtrate was concentrated under reduced pressure. The obtained solid residue was dissolved in acetone (375 ml), Fmoc-Ser(tBu) (36.6 g, 95.5 mmol) was added, and the mixture was stirred at room temperature for 22 hr. Hexane was added to the reaction mixture, and the precipitated solid was collected by filtration and washed with hexane to give the title compound (41.5 g). The mother liquor was concentrated under reduced pressure, and solidified with hexane to give the title compound (5.97 g). yield 47.5 g (86.4%).

(2) Ser(tBu)-ODpm HCl

To a solution of Fmoc-Ser(tBu)-ODpm (16.5 g, 30.0 mmol) in DMF (150 ml) was added 4-dimethylaminopiperidine (18.0 ml, 0.150 mol), and the mixture was stirred at room temperature for 30 min. Ethyl acetate (1.00 l) was added to the reaction mixture, and carbon dioxide was introduced with stirring at room temperature for 10 min. The precipitated solid was filtered off, and the filtrate was washed twice with water, and dried over magnesium sulfate. 0.5N HCl/ethyl acetate (72.0 ml, 36.0 mmol) was added, and the ethyl acetate layer was concentrated under reduced pressure. Hexane was added to the residue, and the precipitate was collected by filtration, and washed with hexane to give the title compound (9.12 g, 83.7%).

(3) Fmoc-Asp(OtBu)-Ser(tBu)-ODpm

Ser(tBu)-ODpm HCl (9.12 g, 25.1 mmol), Fmoc-Asp (OtBu) (10.3 g, 25.1 mmol) and 1-hydroxybenzotriazole (HOBt) (3.56 g, 26.4 mmol) were dissolved in DMF (100 ml), 1-ethyl-3-(3-dimethylaminopropyl)-carbodiimide (EDC) (4.68 ml, 26.4 mmol) was added dropwise with stirring under ice-cooling. After stirring for 30 min under ice-cooling and at room temperature for 18 hr, water was added to the reaction mixture, and the precipitated solid was collected by filtration and washed with water.

This was dissolved in ethyl acetate, and the mixture was washed successively with saturated aqueous sodium hydrogen carbonate, saturated brine, 10% aqueous citric acid and saturated brine, and dried over magnesium sulfate. The ethyl acetate layer was concentrated under reduced pressure, hexane was added to the residue, and the precipitate was collected by filtration to give the title compound (17.7 g, 97.8%).

(4) Asp(OtBu)-Ser(tBu)-ODpm HCl

Fmoc-Asp(OtBu)-Ser(tBu)-ODpm (17.8 g, 24.7 mmol) was dissolved in DMF (125 ml), 4-aminomethylpiperidine (14.8 ml, 0.124 mol) was added, and the mixture was stirred at room temperature for 30 min. Ethyl acetate (1.00 l) was added to the reaction mixture, carbon dioxide was introduced by stirring at room temperature for 10 min. The precipitated solid was filtered off, and the filtrate was washed twice with water, and dried over magnesium sulfate. 0.5N HCl/ethyl acetate (59.3 ml, 29.6 mmol) was added, and the ethyl acetate layer was concentrated under reduced pressure. The oil residue was washed with hexane to give the title compound (12.5 g, 83.7%).

(5) Fmoc-Gly-Asp(OtBu)-Ser (tBu)-ODpm

Asp(OtBu)-Ser(tBu)-ODpm HCl (12.5 g, 20.5 mmol), Fmoc-Gly (6.09 g, 20.5 mmol) and HOBt (2.91 g, 21.5 mmol) were dissolved in DMF (80.0 ml), and EDC (3.81 ml, 21.5 mmol) was added dropwise with stirring under ice-cooling. After mixing for 30 min under ice-cooling and at room temperature for 18 hr, water was added to the reaction mixture, and the precipitated solid was collected by filtration and washed with water. This was dissolved in ethyl acetate, and the mixture was washed successively with saturated aqueous sodium hydrogen carbonate, saturated brine, 10% aqueous citric acid and saturated brine, and dried over magnesium sulfate. The ethyl acetate layer was concentrated under reduced pressure, hexane was added to the solid residue, and the precipitate was collected by filtration to give the title compound (15.1 g, 95.0%).

(6) Gly-Asp(OtBu)-Ser(tBu)-ODpm HCl

Fmoc-Gly-Asp(OtBu)-Ser(tBu)-ODpm (15.1 g, 19.3 mmol) was dissolved in DMF (100 ml), 4-aminomethylpiperidine (11.6 ml, 96.7 mmol) was added, and the mixture was stirred at room temperature for 30 min. Ethyl acetate (800 ml) was added to the reaction mixture, and carbon dioxide was introduced by stirring at room temperature for 10 min.

The precipitated solid was filtered off, and the filtrate was washed twice with water, and dried over magnesium sulfate. 0.5N HCl/ethyl acetate (46.3 ml, 23.2 mmol) was added, and the ethyl acetate layer was concentrated under reduced pressure. The oil residue was washed with hexane to give the title compound (10.1 g, 88.6%).

(7) Fmoc-Arg(Pbf)-Gly-Asp(OtBu)-Ser(tBu)-ODpm

Gly-Asp(OtBu)-Ser(tBu)-ODpm HCl (10.1 g, 16.0 mmol), Fmoc-Arg(Pbf) (10.4 g, 16.0 mmol) and HOBt (2.27 g, 16.8 mmol) were dissolved in DMF (60.0 ml), and EDC (2.98 ml, 16.8 mmol) was added dropwise with stirring under ice-cooling.

After stirring for 30 min under ice-cooling and at room temperature for 18 hr, water was added to the reaction mixture, and the precipitated solid was collected by filtration, and washed with water. This was dissolved in ethyl acetate, and the mixture was washed successively with saturated aqueous sodium hydrogen carbonate, saturated brine, 10% aqueous citric acid and saturated brine, and dried over magnesium sulfate. The ethyl acetate layer was concentrated under reduced pressure, hexane was added to the solid residue, and the precipitate was collected by filtration to give the title compound (18.2 g, 95.8%).

(8) Arg(Pbf)-Gly-Asp(OtBu)-Ser(tBu)-ODpm HCl

Fmoc-Arg(Pbf)-Gly-Asp(OtBu)-Ser(tBu)-ODpm (15.1 g, 19.3 mmol) was dissolved in DMF (100 ml), 4-aminomethylpiperidine (11.6 ml, 96.7 mmol) was added, and the mixture was stirred at room temperature for 30 min. Ethyl acetate (800 ml) was added to the reaction mixture, and carbon dioxide was introduced by stirring at room temperature for 10 min. The precipitated solid was filtered off, and the filtrate was washed twice with water, and dried over magnesium sulfate. 0.5N HCl/ethyl acetate (46.3 ml, 23.2 mmol) was added, and the ethyl acetate layer was concentrated under reduced pressure. The solid residue was reprecipitated from ethyl acetate/hexane to give the title compound (11.3 g, 77.9%).

(9) Boc-Gly-Arg(Pbf)-Gly-Asp(OtBu)-Ser(tBu)-ODpm

Arg(Pbf)-Gly-Asp(OtBu)-Ser(tBu)-ODpm HCl (11.3 g, 10.8 mmol), Boc-Gly (1.89 g, 10.8 mmol) and HOBt (1.53 g, 11.3 mmol) were dissolved in DMF (50.0 ml), EDC (2.00 ml, 11.3 mmol) was added dropwise with stirring under ice-cooling. After stirring for 30 min under ice-cooling and at room temperature for 18 hr, water was added to the reaction mixture, and the precipitated solid was collected by filtration, and washed with water. This was dissolved in ethyl acetate, and the mixture was washed successively with saturated aqueous sodium hydrogen carbonate, saturated brine, 10% aqueous citric acid and saturated brine, and dried over magnesium sulfate. The ethyl acetate layer was concentrated under reduced pressure, hexane was added to the solid residue, and the precipitate was collected by filtration to give the title compound (10.6 g, 87.6%).

(10) Gly-Arg-Gly-Asp-Ser

To Boc-Gly-Arg(Pbf)-Gly-Asp(OtBu)-Ser(tBu)-ODpm (10.5 g, 9.40 mmol) was added 90% aqueous trifluoroacetic acid solution (74.4 ml), and the mixture was stirred at room temperature for 1 hr. Ether was added, and the precipitated solid was collected by filtration.

To this solid was added 90% aqueous trifluoroacetic acid solution (74.4 ml), and the mixture was further stirred at room temperature for 1 hr. Ether was added, and the precipitated solid was collected by filtration, and dissolved in water, and the mixture was freeze-dried. The freeze-dried powder was dissolved in 0.1% aqueous trifluoroacetic acid solution (100 ml), ⅓ amount each thereof was purified by YMC-PakODS column [size: 30×250 mm, elution conditions: flow rate, 20 ml/min; detection, 220 nm; eluent, 1% acetonitrile/0.1% trifluoroacetic acid (30 min)-1-80% acetonitrile/0.1% trifluoroacetic acid (40 min: linear gradient)] to give a freeze-dried product (6.56 g). A solution of the freeze-dried product in 0.5N acetic acid (150 ml) was applied to strong basic ion exchange resin Muromac 1×4 (200 ml, acetic acid type), and eluted with 0.5N acetic acid (400 ml). The eluates were collected and freeze-dried to give the title compound (4.51 g). This was reprecipitated from 1% acetic acid (45 ml)/ethanol (225 ml) to give the title compound (4.12 g).

Amino acid analysis (6N hydrochloric acid, hydrolyzed at 110° C. for 22 hr): Asp 1.00 (1), Ser 0.88 (1), Gly 1.97 (2), Arg 0.99 (1);

elemental analysis: Found C, 39.63; H, 6.39; N, 19.69%

Calculated for $C_{19}H_{30}N_8O_9$ 1.4 $H_2O$ 0.9 $CH_3CO_2H$ C, 39.63; H, 6.44; N, 19.67%.

ESI MS: m/z 491.2 (M+H, 491.2)

Example 2

Synthesis of peptide acid using 1,1-dimethyl-2-phenyl-ethyl (Bpr) group

Synthesis of Fmoc-Val-Gly-Pro-OBpr (1) Z-Pro-OBpr

To a solution of Z-Pro (19.4 g, 77.7 mmol) in DMF (200 ml) were added 2-methyl-1-phenyl-propan-2-ol (12.5 ml, 81.5 mmol) and 4-(dimethylamino)pyridine (DMAP) (2.85 g, 23.3 mmol), EDC HCl (15.6 g, 81.5 mmol) was added under ice-cooling, and the mixture was stirred for 30 min under ice-cooling and further at room temperature overnight. EDC HCl (7.45 g, 38.9 mmol) was added, and the mixture was stirred at room temperature for 4 hr. The reaction mixture was concentrated under reduced pressure, the residue was dissolved in ethyl acetate (400 ml), and the mixture was washed successively with 10% aqueous citric acid solution, water, saturated aqueous sodium hydrogen carbonate solution and water. The organic layer was dried over magnesium sulfate, and concentrated under reduced pressure to give the title compound as a pale-yellow oil (25.4 g, 85.8%).

(2) Fmoc-Gly-Pro-OBpr

Z-Pro-OBpr (3.20 g, 8.39 mmol) was dissolved in methanol (30 ml), 5% Pd-carbon (500 mg) was added, and hydrogen gas was introduced at room temperature for 1 hr. The catalyst was filtered off, and the filtrate was concentrated under reduced pressure. Toluene was added to the residue, and the mixture was concentrated under reduced pressure, which operation was repeated 5 times. The obtained residue, Fmoc-Gly (2.49 g, 8.39 mmol) and HOBt (1.19 g, 8.81 mmol) were dissolved in DMF (20 ml), EDC HCl (1.69 g, 8.81 mmol) was added with stirring under ice-cooling, and the mixture was stirred at room temperature overnight. The reaction mixture was poured into ice water (100 ml), and the mixture was extracted with ethyl acetate (70 ml). The organic layer was washed successively with 2.5% aqueous sodium hydrogen carbonate solution, water, 0.5N aqueous hydrochloric acid, water and saturated brine, and dried over magnesium sulfate. The ethyl acetate layer was concentrated under reduced pressure to give the title compound as a solid (4.10 g, 92.5%).

(3) Fmoc-Val-Gly-Pro-OBpr

Fmoc-Gly-Pro-OBpr (3.00 g, 5.69 mmol) was dissolved in DMF (17 ml), and 4-aminomethylpiperidine (4.36 ml, 56.9 mmol) was added dropwise with stirring under ice-cooling. DMF (20 ml) was added to the reaction mixture, and the mixture was stirred at room temperature for 30 min. Ethyl acetate (300 ml) was added to the reaction mixture, and carbon dioxide was introduced thereinto for 10 min. The precipitated solid was filtered off, and the mixture was washed with ethyl acetate (50 ml×2). The filtrates were collected and washed with water (150 ml×2). The aqueous layer was saturated with sodium chloride, and the mixture was extracted with ethyl acetate (50 ml×2). The organic layers were collected, and dried over magnesium sulfate. 4.7N Hydrochloric acid/dioxane (1.21 ml, 5.69 mmol) was added to the ethyl acetate layer and the mixture was concentrated under reduced pressure to give an oil (yield 85% by HPLC detection). The obtained oil (4.84 mmol), Fmoc-Val (1.72 g, 5.08 mmol) and HOBt (0.719 g, 5.32 mmol) were dissolved in DMF (25 ml), and EDC (0.974 ml, 5.32 mmol) was added dropwise with stirring under cooling (−10° C.). After stirring at room temperature overnight, the reaction mixture was poured into ethyl acetate (200 ml) and water (200 ml), and partitioned. The ethyl acetate layer was washed successively with 2.5% aqueous sodium hydrogen carbonate solution, water and saturated brine, and dried over magnesium sulfate. The ethyl acetate layer was concentrated under reduced pressure, and the residue was crystallized from ether-hexane to give the title compound (2.41 g, 80.9%). When Fmoc-Val-Gly-Pro-OBpr (1.0 mg) was treated with trifluoroacetic acid (100 µl), the Bpr group was completely cleaved at room temperature in 15 min.

Example 3

Synthesis of peptide carboxamide using 2,4-dimethoxybenzyl (Dmb)

Synthesis of Melanocyte Stimulating Hormone-Release Inhibitory Factor (MIF: Pro-Leu-Gly-NH$_2$)

(1) Fmoc-Gly-NHDmb 2,4-Dimethoxybenzylamine (4.54 g, 27.1 mmol) was dissolved in DMF (60 ml), and 4.7N hydrochloric acid/dioxane (5.76 ml, 27.1 mmol) was added while stirring under ice-cooling. Thereto were added Fmoc-Gly (8.07 g, 27.1 mmol) and HOBt (3.66 g, 27.1 mmol), EDC (4.95 ml, 27.1 mmol) was added dropwise with stirring under ice-cooling, and the mixture was stirred at room temperature overnight. The reaction mixture was poured into ice water (500 ml), and the mixture was extracted with ethyl acetate. The ethyl acetate layer was concentrated under reduced pressure, isopropylethylether and hexane were added to the precipitated crystals, and the precipitate was collected by filtration. This was recrystallized from ethyl acetate/isopropylethylether to give the title compound (11.3 g, 93.5%).

(2) Gly-NHDmb HCl

A solution of Fmoc-Gly-NHDmb (5.00 g, 11.2 mmol) in DMF (50 ml) was ice-cooled, 4-aminomethylpiperidine (13.4 ml, 0.112 mol) was added, and the mixture was stirred for 30 min. Chloroform (450 ml) was added to the reaction mixture, and the mixture was stirred at room temperature while introducing carbon dioxide for 30 min. The precipitated solid was filtered off, and the filtrate was washed with water, and dried over magnesium sulfate. To the ice-cooled ethyl acetate layer was added 4.7N hydrochloric acid/dioxane (4.77 ml, 22.4 mmol), and the mixture was concentrated under reduced pressure. Isopropylethylether was added to the residue to allow crystallization to give the title compound (2.82 g, 96.6%).

(3) Fmoc-Leu-Gly-NHDmb

Gly-NHDmb HCl (2.69 g, 10.3 mmol), Fmoc-Leu (3.82 g, 10.8 mmol) and HOBt (1.46 g, 10.8 mmol) were dissolved in DMF/NMP (1:1, 50 ml), and EDC (1.98 ml, 10.8 mmol) was added dropwise with stirring under ice-cooling. The mixture was further stirred at room temperature for 1.5 hr, and poured into water (400 ml). The liberated oil was extracted with ethyl acetate (50 ml×2), and the extract was washed successively with saturated aqueous sodium hydrogen carbonate solution, water, 10% aqueous citric acid solution, water and saturated brine, dried over magnesium sulfate, and concentrated under reduced pressure. Ether was added to the oily residue to allow crystallization to give the title compound (2.99 g, 51.9%).

(4) Leu-Gly-NHDmb HCl

A solution of Fmoc-Leu-Gly-NHDmb (2.00 g, 3.60 mmol) in DMF (20 ml) was ice-cooled, 4-aminomethylpiperidine (4.30 ml, 36.0 mmol) was added, and the mixture was stirred for 30 min. Ethyl acetate (200 ml) was added to the reaction mixture, and carbon dioxide was introduced for 1 hr at room temperature. The precipitated solid was collected by filtration, and the filtrate was washed with water. The solid collected by filtration was suspended in chloroform, and the precipitate was collected by filtration. The chloroform layer was concentrated, and the residue was dissolved in ethyl acetate. The ethyl acetate layers were collected, washed with water, and dried over magnesium sulfate. The ethyl acetate layer was concentrated under reduced pressure, and isopropylethylether was added to the oily residue to allow crystallization to give the title compound (0.95 g, 70.4%).

(5) Boc-Pro-Leu-Gly-NHDmb

Leu-Gly-NHDmb HCl (0.70 g, 1.9 mmol), Boc-Pro (0.45 g, 2.1 mmol) and HOBt (0.28 g, 2.1 mmol) were dissolved in DMF (10 ml), and EDC (0.38 ml, 2.1 mmol) was added with stirring under ice-cooling. After stirring at room temperature overnight, the mixture was poured into water (80 ml), and the liberated oil was extracted with ethyl acetate. The organic layer was washed successively with saturated aqueous sodium hydrogen carbonate solution, water, 10% aqueous citric acid and water, and dried over magnesium sulfate. The ethyl acetate layer was concentrated under reduced pressure, and isopropylethylether was added to the oily residue to allow crystallization to give the title compound (0.84 g, 82%).

(6) Pro-Leu-Gly-NH$_2$CH$_3$CO$_2$H

Boc-Pro-Leu-Gly-NHDmb (0.50 g, 0.94 mmol) was treated with 1 M trifluoromethanesulfonic acid-thioanisole/trifluoroacetic acid (21 ml) in the presence of m-cresol (2.0 ml) under ice-cooling for 2 hr. To the reaction mixture were added ether and isopropylethylether, and the precipitate was collected by filtration. The powder was dissolved in a small amount of trifluoroacetic acid, and ether and isopropylethylether were added to allow re-precipitation. The crude peptide was purified by HPLC using an ODS column (30×250 mm) (eluent A=0.1% TFA/water, B=0.1% TFA/acetonitrile, elution gradient A:B=95.5:0.5-85:15 (80 min linear gradient)) to give the title compound in a free form (0.27 g). This was dissolved in 1% aqueous acetic acid solution (15 ml), and the mixture was applied to a strong basic ion exchange resin Muromac 1×4 (acetic acid type, 15 ml) column. Further, elution with 1% aqueous acetic acid solution (80 ml) was performed, and the eluate was freeze-dried to give the title compound (0.22 g, 68.1%).

ESI MS: m/z 285.2 (M+H, 285.3)

Example 4

Synthesis of peptide carboxamide using bis(4-methoxyphenyl)methyl [CH(PhOMe)$_2$] group Synthesis of Melanocyte Stimulation Hormone-Release Inhibitory Factor (MIF: Pro-Leu-Gly-NH$_2$)

(1) Fmoc-Gly-NHCH(PhOMe)$_2$

A solution of Fmoc-Gly (6.43 g, 21.6 mmol), HCTU (8.79 g, 21.2 mmol) and 6-Cl-HOBt (3.59 g, 21.2 mmol) in DMF (40 ml) was stirred with cooling at −5° C. To this solution was added DIEA (7.00 ml, 41.2 mmol), and bis(4-methoxyphenyl)methylamine/DMF (40 ml) solution was added 2 min later. The reaction mixture was stirred at room temperature overnight. Water was poured into the reaction mixture, and the precipitated solid was collected by filtration, and washed with water. The solid was dissolved in chloroform/methanol (3:1, v/v), and ether was added to allow re-precipitation to give the title compound (9.88 g, 91.9%).

(2) Gly-NHCH(PhOMe)$_2$ HCl

A solution of Fmoc-Gly-NHCH(PhOMe)$_2$ (9.53 g, 18.2 mmol) in DMF (80 ml) was ice-cooled, 4-aminomethylpiperidine (21.8 ml, 0.182 mol) was added, and the mixture was stirred for 30 min. Ethyl acetate (600 ml) was added to the reaction mixture, and carbon dioxide was introduced for 10 min with stirring at room temperature. The precipitated solid was filtered off, and the filtrate was washed twice with water, and dried over magnesium sulfate. 4.7N HCl/dioxane (7.74 ml, 31.4 mmol) was added, and the ethyl acetate layer was concentrated under reduced pressure. Ether was added to the solid residue, and the precipitate was collected by filtration. Recrystallization from ethyl acetate-isopropyl ether gave the title compound (5.02 g, 81.9%).

(3) Fmoc-Leu-Gly-NHCH(PhOMe)$_2$

Gly-NHCH(PhOMe)$_2$ HCl (4.72 g, 14.0 mmol), Fmoc-Leu (5.20 g, 14.7 mmol) and HOBt (1.99 g, 14.7 mmol) were dissolved in DMF (60 ml), and EDC (2.69 ml, 14.7 mmol) was added dropwise with stirring under ice-cooling. After stirring at room temperature for 3 hr, water was poured into the reaction mixture. The precipitated solid was collected by filtration, and washed with water. The solid was recrystallized from ethyl acetate-hexane to give the title compound (10.5 g*, 117%) (*solvent is attached).

(4) Leu-Gly-NHCH(PhOMe)$_2$ HCl

A solution of Fmoc-Leu-Gly-NHCH(PhOMe)$_2$ (9.74 g, 13.0 mmol) in DMF (60 ml) was ice-cooled, 4-aminomethylpiperidine (15.6 ml, 0.130 mol) was added, and the mixture was stirred for 30 min. Ethyl acetate (500 ml) was added to the reaction mixture, and carbon dioxide was introduced with stirring for 10 min at room temperature. The precipitated solid was filtered off, and the filtrate was washed twice with water, and dried over magnesium sulfate. 4.7N HCl/dioxane (5.53 ml, 26.0 mmol) was added, and the ethyl acetate layer was concentrated under reduced pressure. The oily residue was crystallized from ether and recrystallized from ethyl acetate-ether to give the title compound (5.09 g, 87.0%).

(5) Boc-Pro-Leu-Gly-NHCH(PhOMe)$_2$

Leu-Gly-NHCH(PhOMe)$_2$ HCl (2.25 g, 5.00 mmol), Boc-Pro (1.18 g, 5.50 mmol) and HOBt (0.740 g, 5.50 mmol) were dissolved in DMF (30 ml), and EDC (1.01 ml, 5.50 mmol) was added dropwise with stirring under ice-cooling. After stirring at room temperature for 2 hr, water was poured into the reaction mixture. The liberated oil was extracted with ethyl acetate. The organic layer was washed successively with water, saturated aqueous sodium hydrogen carbonate solution, water, 10% aqueous citric acid and water, and dried over magnesium sulfate. The ethyl acetate layer was concentrated under reduced pressure, and isopropyl ether was added to the oily residue to allow crystallization to give the title compound (2.72 g, 89.2%).

(6) Pro-Leu-Gly-NH$_2$CH$_3$CO$_2$H

Boc-Pro-Leu-Gly- NHCH(PhOMe)$_2$ (0.50 g, 0.82 mmol) was treated with trifluoroacetic acid (9.5 ml) in the presence of triisopropylsilane (0.25 ml) and water (0.25 ml) at room temperature for 5 hr. The reaction mixture was concentrated under reduced pressure, ether was added to the oily residue, and the precipitate was collected by filtration. This powder was dissolved in water, and the mixture was freeze-dried to give crude peptide (0.35 g). The crude peptide was purified by HPLC using an ODS column (30×250 mm) (eluent A=0.1% TFA/water, B=0.1% TFA/acetonitrile, elution gradient A:B=95.5:0.5 to 85:15, 80 min linear gradient) to give the title compound in a free form (0.26 g). This was dissolved in 1% aqueous acetic acid solution (10 ml), and the mixture was applied to a strong basic ion exchange resin Muromac (acetic acid type, 10 ml) column. The residue was further eluted with 1% aqueous acetic acid solution (70 ml) and the eluate was freeze-dried to give the title compound (0.23 g, 81%).

ESI MS: m/z 285.2 (M+H, 285.3)

INDUSTRIAL APPLICABILITY

The method of the present invention can be preferably utilized for industrial production of peptide pharmaceutical products and the like.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for removal of a dibenzofulvene amine adduct from a reaction mixture obtained by reacting, for deprotection, an amino acid compound protected with an Fmoc group with an amine compound containing a nitrogen atom which is bonded to at least one hydrogen atom, said method comprising:
(i) adding carbon dioxide to said reaction mixture, to obtain a carbonate of said dibenzofulvene amine adduct; and
(ii) removing said carbonate of said dibenzofulvene amine adduct from said reaction mixture.

2. A method for removal of dibenzofulvene, produced by deprotection of an amino acid compound protected with an Fmoc group, from a reaction mixture, which comprises:
(i) mixing a reaction mixture formed by deprotection of an amino acid compound protected with an Fmoc group with an amine compound containing a nitrogen atom which is bonded to at least one hydrogen atom to give a mixture containing a dibenzofulvene amine adduct;
(ii) adding carbon dioxide to said mixture, to obtain a carbonate of said dibenzofulvene amine adduct; and
(iii) removing said carbonate of said dibenzofulvene amine adduct from said reaction mixture.

3. A method for removal of a dibenzofulvene amine adduct from a reaction mixture obtained by reacting, for deprotection, an amino acid compound protected with an Fmoc group with an amine compound containing a nitrogen atom which is bonded to at least one hydrogen atom, said method comprising:
(i) contacting said reaction mixture with carbon dioxide, to obtain a carbonate of said dibenzofulvene amine adduct; and
(ii) removing said carbonate of said dibenzofulvene amine adduct from said reaction mixture by precipitating said carbonate of said dibenzofulvene amine adduct in a solvent containing at least one member selected from the group consisting of acetic acid ester, chloroform, methylene chloride, tetrahydrofuran, acetonitrile, acetone, ether, and a mixture thereof.

4. A method according to claim 3, further comprising removing said carbonate of said dibenzofulvene amine adduct by filtration.

5. A method according to claim 1, wherein said amine compound containing a nitrogen atom which is bonded to at least one hydrogen atom is a diamine.

6. A method according to claim 5, wherein said amine compound containing a nitrogen atom which is bonded to at least one hydrogen atom is selected from the group consisting of 4-aminomethylpiperidine, 4-dimethylaminopiperidine, 1,5-diaminopentane and 1,2-diaminocyclohexane.

7. A method according to claim 1, wherein said amino acid compound protected with an Fmoc group is an amino acid ester protected with an Fmoc group, an amino acid amide protected with an Fmoc group, or a peptide protected with an Fmoc group.

8. A method of producing a peptide by a liquid phase synthesis method, comprising removing a dibenzofulvene amine adduct from a reaction mixture obtained by reacting, for deprotection, an amino acid compound protected with an Fmoc group with an amine compound containing a nitrogen atom which is bonded to at least one hydrogen atom,
by a method comprising:
(i) adding carbon dioxide to said reaction mixture, to obtain a carbonate of said dibenzofulvene amine adduct; and
(ii) removing said carbonate of said dibenzofulvene amine adduct from said reaction mixture.

9. A method according to claim 8, comprising:
(1) condensing a C-protected peptide, a C-protected amino acid, or a C-protected amino acid amide with an N-Fmoc amino acid in the presence of a condensing agent; and/or
(2) condensing a C-protected peptide, a C-protected amino acid, or a C-protected amino acid amide with an N-Fmoc amino acid activated ester.

10. A method according to claim 9, wherein said condensing a C-protected peptide, a C-protected amino acid, or a C-protected amino acid amide with N-Fmoc amino acid in the presence of a condensing agent, (1), is performed in the further presence of an activator.

11. A method according to claim 9, wherein an intermediate peptide obtained by a method which comprises reacting an amino acid compound protected with an Fmoc group with an amine compound containing a nitrogen atom which is bonded to at least one hydrogen atom, to obtain an intermediate peptide, without isolation as a solid, is:
(1) condensed with N-Fmoc amino acid in the presence of a condensing agent; and/or
(2) condensed with an N-Fmoc amino acid activated ester.

12. A method according to claim 8, which is performed as a one-pot synthesis.

13. A method for preparation of a peptide, comprising:
(i) reacting a first amino acid compound which is N-protected with an Fmoc group with a second amino acid compound which is N-unprotected, to obtain a third amino acid compound which is N-protected with an Fmoc group;
(ii) reacting said third amino acid compound with an amine compound containing a nitrogen atom which is bonded to at least one hydrogen atom to give a first reaction mixture which comprises a fourth amino acid compound which is N-unprotected and a dibenzofulvene amine adduct;
(iii) adding carbon dioxide to said first reaction mixture, to obtain a second reaction mixture which comprises said fourth amino acid compound which is N-unprotected and a carbonate of said dibenzofulvene amine adduct;
(iv) removing said carbonate of said dibenzofulvene amine adduct from said second reaction mixture, to obtain a third reaction mixture which comprises said fourth amino acid compound which is N-unprotected; and
(v) reacting said fourth amino acid compound which is N-unprotected with a fifth amino acid compound which is N-protected with an Fmoc group to obtain a sixth amino acid compound which is N-protected with an Fmoc group.

14. A method according to claim 13, comprising precipitating said carbonate of said dibenzofulvene amine adduct in a solvent containing at least one member selected from the group consisting of acetic acid ester, chloroform, methylene chloride, tetrahydrofuran, acetonitrile, acetone, ether, and a mixture thereof.

15. A method according to claim 13, comprising removing said carbonate of said dibenzofulvene amine adduct by filtration.

16. A method according to claim 13, wherein said amine compound containing a nitrogen atom which is bonded to at least one hydrogen atom is a diamine.

17. A method according to claim 13, wherein said amine compound containing a nitrogen atom which is bonded to at least one hydrogen atom is selected from the group consisting of 4-aminomethylpiperidine, 4-dimethylaminopiperidine, 1,5-diaminopentane and 1,2-diaminocyclohexane.

18. A method according to claim 13, wherein said first amino acid compound which is N-protected with an Fmoc group is an amino acid ester protected with an Fmoc group, an amino acid amide protected with an Fmoc group, or a peptide protected with an Fmoc group.

19. A method according to claim 13, wherein said fifth amino acid compound which is N-protected with an Fmoc group is an amino acid ester protected with an Fmoc group, an amino acid amide protected with an Fmoc group, or a peptide protected with an Fmoc group.

20. A method according to claim 13, wherein said second amino acid compound which is N-unprotected is a C-protected peptide, a C-protected amino acid, or a C-protected amino acid amide.

21. A method according to claim 1, wherein said adding carbon dioxide to said reaction mixture is conducted by: (a) blowing carbon dioxide gas into said reaction mixture, (b) adding carbonated water to said reaction mixture, or (c) adding dry ice to said reaction mixture.

22. A method according to claim 2, wherein said adding carbon dioxide to said reaction mixture is conducted by: (a) blowing carbon dioxide gas into said reaction mixture, (b) adding carbonated water to said reaction mixture, or (c) adding dry ice to said reaction mixture.

23. A method according to claim 8, wherein said adding carbon dioxide to said reaction mixture is conducted by: (a) blowing carbon dioxide gas into said reaction mixture, (b) adding carbonated water to said reaction mixture, or (c) adding dry ice to said reaction mixture.

24. A method according to claim 13, wherein said adding carbon dioxide to said first reaction mixture is conducted by: (a) blowing carbon dioxide gas into said first reaction mixture, (b) adding carbonated water to said first reaction mixture, or (c) adding dry ice to said first reaction mixture.

* * * * *